United States Patent [19]

Hafner et al.

[11] Patent Number: 4,532,208
[45] Date of Patent: Jul. 30, 1985

[54] CONSTITUTIVE GLUCOSE ISOMERASE PRODUCER

[75] Inventors: Edmund W. Hafner, Arlington Heights; Denise M. Jackson, Chicago, both of Ill.

[73] Assignee: UOP Inc., Des Plaines, Ill.

[21] Appl. No.: 491,835

[22] Filed: May 5, 1983

[51] Int. Cl.³ .................. C12P 19/24; C12N 9/92; C12N 1/20; C12R 1/465

[52] U.S. Cl. .................. 435/94; 435/234; 435/253; 435/886

[58] Field of Search .................. 435/94, 234, 253

[56] References Cited

U.S. PATENT DOCUMENTS

Re. 29,152  3/1977  Armbruster .................. 195/31
3,816,259   6/1974  Collinge et al. .................. 435/207
4,355,103  10/1982  Boguslawski et al. .................. 435/234

OTHER PUBLICATIONS

W.-P. Chen, Process Biochemistry, Jun./Jul. 1980, pp. 30–35.

Primary Examiner—Lionel M. Shapiro
Attorney, Agent, or Firm—James R. Hoatson, Jr.; Eugene I. Snyder; William H. Page, II

[57] ABSTRACT

A mutant Streptomyces coelicolor, NRRL 15398, produces glucose isomerase constitutively at a level at least as great as the parent does inductively in common growth media. The isomerase can be effectively used to isomerize glucose to fructose in a continuous process using immobilized enzyme.

7 Claims, No Drawings

CONSTITUTIVE GLUCOSE ISOMERASE PRODUCER

Glucose isomerase, sometimes referred to as xylose isomerase, catalyzes the reversible isomerization of glucose to fructose. Fructose long has been recognized as a good alternative to sugar (sucrose) because of its relatively high sweetness and other desirably physical, chemical, and physiological properties, and the use of glucose isomerase to convert glucose in corn syrup to fructose has been practiced for some time. Although the production of high fructose corn syrup is concentrated in the United States, plant capacity in Europe and the Far East has been steadily increasing.

The enzyme glucose isomerase occurs widely in nature and is produced by such genera as Pseudomonas, Lactobacillus, Actinoplanes, Arthrobacter, Bacillus, and Streptomyces, with the latter species being perhaps the most important commercial source of the enzyme. W.-P. Chen, *Process Biochemistry*, June/July, 1980, pages 30–35. The need for improving glucose isomerase (GI) production over that found in wild-type microorganisms has spurred many efforts to produce mutants with improved characteristics. For example, U.S. Pat. No. Re. 29,152 describes mutants of Streptomyces olivochromogenes which have the characteristics of (1) producing GI in the absence of xylose (i.e., the enzyme is constitutive), but (2) exhibits greater GI production in the presence of xylose (i.e., enzyme production is induced, at least in part), and (3) in the presence of xylose the mutant produces more GI than the parent.

A desirable GI producing microorganism would produce the enzyme constitutively, that is, the microorganism would elaborate GI when grown on a medium free of xylose. This is advantageous because of the relatively high cost of xylose. A desirable GI producer also should be characterized by relatively high enzyme production, especially as measured by GI activity per unit of dry weight cells. Additionally, such a GI produced should show a high growth rate, so as to have high enzyme production per unit time. Lastly, it is desirable that the GI producer should grow well in common, inexpensive media, that is, growth requirements for the microorganism should be such that relatively inexpensive sources of carbon, nitrogen, and minerals can be used.

We have discovered a mutant of Streptomyces coeliecolor possessing the aforementioned desirable and advantageous properties. In particular, the mutant described herein produces GI constitutively. The mutant also produces at least as much GI in the absence of xylose as in the presence of that sugar. Additionally, the mutant produces at least as much GI, possibly more, in the absence of xylose than does the parent strain in the presence of xylose. The mutant described herein grows well in common media and has no unusual growth requirements.

SUMMARY OF THE INVENTION

In one aspect the invention herein is a biologically pure culture of mutant microorganisms of Streptomyces coelicolor having the ability to produce a glucose isomerase as a constitutive enzyme when the mutant microorganisms are grown aerobically in a medium of an assimilable source of carbon, nitrogen, and mineral nutrients at a temperature from about 20° C. to about 45° C. A more specific embodiment is a biologically pure culture of mutant Streptomyces coelicolor NRRL 15398. Another aspect of the invention herein is a method of producing a glucose isomerase comprising cultivating Streptomyces coelicolor NRRL 15398 in a nutrient medium for a time sufficient to produce a recoverable quantity of the isomerase. In still another aspect the invention is a method of converting glucose to fructose comprising contacting an aqueous solution containing glucose with a glucose isomerase from Streptomyces coelicolor NRRL 15398 at a temperature from about 40° C. to about 80° C. at a pH between about 6.5 and about 9.5 for a time sufficient to effect the isomerization of glucose to fructose, and recovering the formed fructose.

DESCRIPTION OF THE INVENTION

The essence of the invention described herein is the induction and selection of a mutant Streptomyces coelicolor which produces GI constitutively in an amount at least as great as does the parent when the latter is grown in the presence of xylose.

The parent strain of the mutant of this invention is Streptomyces coelicolor ATCC 21666. Mutagenesis was carried out using three separate, successive treatments with ethyl methanesulfonate, EMS, although other mutagens may be used but not necessarily with equivalent results. After the mutagenesis treatments liquid cultures were grown in the absence of xylose and a sample was plated out on agar, also in the absence of xylose. Colonies were assayed for constitutive GI production. In this way there was obtained the mutant, NRRL 15398, which is the subject of this invention.

The mutant microorganism NRRL 15398 produces GI in the absence of xylose as an inducer and at levels greater than 1000 units per gram of dry cells under optimum conditions. It appears to produce no additional enzyme, perhaps even somewhat less GI, in the presence of xylose. The production of GI by the mutant is repressed by glucose but is relatively unaffected by the presence of other monosaccharides and disaccharides. Glucose isomerase production also is inhibited by 2-deoxyglucose. The mutant microorganism grows well using a broad variety of nitrogen sources with the exception of beet molasses which shows an extremely inhibitory effect. There is also no sign of growth when sodium caseinate is the sole nitrogen source. There were no observable morphological differences between the parent and mutant strains on a variety of different agar media.

EXAMPLE 1—Mutagenesis

The maintenance medium for the parent strain of Streptomyces coelicolor, ATCC 21666, and all mutants obtained therefrom consisted of 1% yeast autolysate, 1% caseine enzymatic hydrolysate, 0.5% beef extract, 1 millimolar magnesium sulfate, and 0.05M potassium phosphate. The pH of the medium was adjusted to 7.00 with sodium hydroxide before autoclaving. Bacteria were transferred regularly onto a 2% agar medium containing the above ingredients as an inoculum for liquid cultures. The strains were generally incubated for 48 hours in a liquid culture at 30° C. with agitation (200 rpm) in a New Brunswick Controlled Environment Shaker.

After 48 hours, the 50 ml cultures (contained in 250 ml baffled Erlenmeyer flasks) were harvested and washed free of spent culture broth by centrifugation (4° C. at 15,000 rpm for 10 minutes). The cell pellet was frozen with a dry ice-acetone mixture and dried to a powder under vacuum on a Virtis lyophilizer. The dry cell weight was measured and the cells resuspended in 30 ml of 0.02M potassium phosphate buffer, pH 7.0, containing 0.85% sodium chloride. This material was sonicated for 1 minute at low powder with a Labline sonifier.

For the glucose isomerase assay procedure 0.2 ml of the sonicated cell slurry was diluted to 1 ml with distilled $H_2O$. This 1 ml sample was added to 3 mls of the substrate solution which consists of 45% fructose (W/V) 0.05M imidazole buffer at pH 9.5, $5 \times 10^{-3}$M $MgSo_4$, and $5 \times 10^{-4}$M $CoCl_2$. After thorough mixing, the reaction mixture was incubated at 60° C. for a 60 minute duration. The reaction was terminated by quenching with the addition of 1 ml of 0.1N HCl, again thoroughly mixing, and chilling with ice. The enzyme activity was determined by measurement of glucose concentration using a Beckman Glucose Analyzer. One unit of GI activity is equivalent to the formation of $1\mu$ mole of glucose per ml per minute.

Mutagenesis was begun using the parent strain Streptomyces coelicolor ATCC 21666, in a liquid culture broth for approximately 24 hours. Ten ml of the culture was washed free of broth under sterile conditions and the wet cell pellet was resuspended in 10 ml of 0.2M tris(hydroxymethylamino)methane hydrochloride at a pH of 7.5. Ethyl methanesulfonate was added to the cell suspension in a concentration of 0.15 ml per 10 ml suspension and the cells were then incubated, with agitation, at 30° C. for 2.5 hours. After this time the EMS treated cells were added to 50 ml of the maintenance medium and permitted to grow for 48 hours. Three mutagenic treatments were performed before the mutagenized cells were screened.

Screening of the mutagenized cells involved transferring the organisms from liquid cultures to agar plates so that individual colonies could be evaluated for enzyme production. To achieve this, 2.5 ml aliquots of the liquid culture were briefly (10 seconds) sonicated at low power. This procedure breaks up the mycelial strands and releases individual mutated cells. These aliquots were then recombined and diluted to a concentration of 40% glycerol and stored at $-70°$ C. until used.

Dilutions of these EMS treated cells were then plated unto an agar medium to give approximately 200 colonies per plate. These colonies were assayed for constitutive production of glucose isomerase. The mutant microorganism Streptomyces coelicolor NRRL 15398 was found by this procedure. Comparison of GI production by the parent and mutant strains are shown in the accompanying table.

TABLE 1

Comparison of GI Production

| Microorganism | 1% Xylose | GI, units/g dry cells |
|---|---|---|
| ATCC 21666, parent | present | 970 |
|  | absent | 280 |
| NRRL 15398, mutant | present | 1040 |
|  | absent | 1230 |

EXAMPLE 2—Mutant Characteristics

Streptomyces coelicolor NRRL 15398 was grown in the presence of monosaccharides and disaccharides. The control received no additional carbohydrates over the maintenance medium. The sugars were added separately at a total of 1% concentration to the medium after sterilization and GI production was measured as described above. Results are shown in Tables 2 and 3, the latter displaying the effect of glucose analogs on GI production.

TABLE 2

Effect of Carbohydrates on GI Production by Mutant, NRRL 15398

| Carbohydrate | GI, units/g dry cells |
|---|---|
| xylose | 600 |
| sucrose | 770 |
| glucose | 230 |
| lactose | 480 |
| maltose | 640 |
| fructose | 430 |
| galactose | 510 |
| control | 530 |

TABLE 3

Effect of Glucose and Glucose Analogs on GI Production by NRRL 15398

| Addend | GI, units/g dry cells |
|---|---|
| control | 870 |
| glucose (1.0%) | 300 |
| 2-deoxyglucose (1.0%) | 380 |
| 3-O—methylglucoside (1.0) | 640 |

Table 4 shows the effect of different nitrogen sources in the medium on GI production. Corn steep liquor produced the highest specific activity whereas beet molasses had an extremely inhibitory effect. No significant growth was obtained with sodium caseinate alone.

TABLE 4

Effect of Nitrogen Source on GI Production by NRRL 15398

| Nitrogen Source (2% W/V) | GI, units/g dry cells |
|---|---|
| Yeast extract, Anheuser Busch | 880 |
| Yeast extract, Difco | 1030 |
| Yeast extract, BBL | 1030 |
| Yeast autolysate, Sigma | 980 |
| Beet molasses | 30 |
| Corn steep liquor, Archer-Daniels Midland | 1190 |
| Soy flour | 740 |
| Casein enzymatic hydrolysate, Sigma | 890 |
| Peptone, Difco | 910 |
| Tryptone, Difco | 440 |
| Sodium caseinate | no significant growth |

Table 5 shows the results of an attempt to further increase GI production in the mutant using the corn steep liquor medium described in the prior table. Yeast autolysate was added in concentrations ranging from 0 to 2%. Addition of any amount of yeast autolysate to the rich corn steep liquor medium decreases the enzyme production.

TABLE 5

Effect of Yeast Autolysate on GI Production by NRRL 15398 in 1% Corn Steep Liquor Medium

| % Yeast Autolysate | GI, units/g dry cells |
|---|---|
| 0 | 1800 |
| 0.5 | 1490 |
| 1.0 | 1520 |
| 1.5 | 1170 |
| 2.0 | 1140 |

Table 6 describes some general morphological characteristics of the colonies of the parent and mutant strains on different agar media. Three rich media and a minimal medium containing different carbohydrates as the carbon source were investigated. In all media tested there were no observable differences between the parent and mutant strains in this regard.

TABLE 6

Growth and Morphology Characteristics

| | ATCC 21666 | NRRL 15398 |
|---|---|---|
| Maintenance medium plus: | | |
| Sabouraud dextrose agar | growth similar to maintenance medium; less aerial mycelium formation; forms higher colonies | growth similar to maintenance medium; less aerial mycelium formation; forms higher colonies |
| Tryptic soy agar and glucose | growth identical to maintenance medium | growth identical to maintenance medium |
| Nutrient agar | growth similar to maintenance medium; less aerial mycelium formation | growth similar to maintenance medium; less aerial mycelium formation |
| Minimal media: | Bacto Yeast Nitrogen Base (without amino acids) plus $(NH_4)_2 SO_4$ plus carbohydrate | |
| Carbohydrate (1.92%) | | |
| Glucose | flat colonies; no aerial mycelia; slight yellow pigmentation | identical to parent strain |
| Sorbose | very poor growth | identical to parent strain |
| Maltose | flat colonies, no aerial mycelia; slight yellow pigmentation | identical to parent strain |
| Sucrose | flat colonies; no aerial mycelia; slight yellow pigmentation | identical to parent strain |
| Xylose | very poor growth | very poor growth |
| Fructose | flat colonies; no aerial mycelia; yellow pigmentation | identical to parent strain |
| Glycerol | flat colonies; no aerial mycelia; yellow pigmentation | identical to parent strain |

Glucose isomerase can be released from cells of Streptomyces coelicolor NRRL 15398 by a variety of methods, including sonication, enzyme digestion of the cell wall, and grinding including homogenization. Solids are then removed, as by centrifugation. The enzyme may be purified by a variety of methods, including merely heat treatment (see, for example, U.S. Pat. No. 4,250,263) and precipitation with isopropyl alcohol. The glucose isomerase produced has a molecular weight of about 220,000. The subunits were determined using the standard SDS gel electrophoresis technique (Weber and Osborn, *J. Biol. Chem.*, 244, 4406 (1969)) and had a molecular weight of approximately 38,500. In the isomerization of glucose to fructose, a temperature from about 40° C. to about 80° C. may be used, although the interval between about 50° and 65° C. is preferred. At a temperature of about 60° C. the enzyme is active at a pH from about 6.5 to about 9.5, with optimum activity displayed in the range from about 7.5 to about 8.5. At 60° C. and pH of about 8.0 the enzyme has a half-life of about 60 days.

EXAMPLE 3—Enzyme Characterization

Whole cells from a culture were harvested and washed free of the spent medium. Sonication with a Branson sonifier can be done on previously freeze-dried cells or on the harvested cell cake. The cells were suspended in a buffer solution of 0.05M Imidazole at pH 7.5, 1 mM $MgSO_4$ and 10% glycerol. Sonication was performed until the cells were ruptured, the cell debris was removed by centrifugation at 12,000 rpm, and the supernatant (crude extract) was decanted. The crude extract was then heated for 10 min. at 60° C. and centrifuged for 20 min. at 10,000 rpm. To the supernatant containing the enzyme was added isopropanol to a total concentration of 44–55% at a temperature of about 0° C. Enzyme which precipitated was collected by centrifugation, and stored, if necessary, in a 0.05M imidazole buffer at pH 7.5 containing 1 mM $MgSO_4$.

The molecular weight of the glucose isomerase produced was determined from column (1.5×90 cm) chromatography on Sephadex G 150 using a 0.05M imidazole buffer at pH 7.0 containing 5 mM magnesium ion, 0.5 mM divalent cobalt ion, and 0.2M potassium chloride at a flow rate of about 1 ml per hour. A calibration curve of elution volume versus molecular weight was constructed using as standards lysozyme, trypsin, ovalbumin dimer, bovine serum albumin dimer, and catalase.

The subunit molecular weight was determined by gel electrophoresis. The enzyme solution in 0.1M phosphate buffer, pH 7.1, was dialyzed against a large volume of the same buffer containing 1% sodium dodecyl sulfate (SDS) and 1% 2-mercaptoethanol (ME). The protein solution containing 1% each of SDS and ME was heated at 100° C. for 5–10 minutes to denature the protein, and the denatured solution was then dialyzed against a large volume of the aforementioned buffer containing 0.1% each of SDS and ME. The resulting solution of denatured protein in 0.1M phosphate buffer at pH 7.1 containing 0.1% SDS and 0.1% ME was subjected to gel electrophoresis on a 10% polyacrylamide gel standards of bovine serum albumin, catalase, ovalbumin, trypsin, myoglobin, and lysozyme as well as the GI subunits in question were run at 8 milliamperes per gel. A plot of molecular weight versus mobility afforded a molecular weight of about 38,500 for the subunits.

The glucose isomerase from Streptomyces coelicolor NRRL 15398 may be used to isomerize glucose to fructose either homogeneously or, preferably, heterogeneously. Because of all the advantages coming from enzyme reuse, it is desirable to use a continuous process with an immobilized glucose isomerase. The support matrix of Levy and Fusee, U.S. Pat. No. 4,141,857 is especially useful. Such support matrices are refractory, porous inorganic oxides impregnated with polyamines subsequently cross-linked with polyfunctional reagents so as to furnish pendant functional groups. When contacted with glucose isomerase the enzyme reacts with such pendant functional groups so as to form an immobilized enzyme system where the enzyme is attached to the support matrix by covalent bonds. A continuous process using a fixed bed of an immobilized glucose isomerase is the preferred method of forming fructose from glucose using GI. The process may be carried out at a temperature from between 40° to about 80° C., but most preferably at a temperature between about 50° and about 65° C. The isomerization may be carried out with a GI from the mutant of this invention at a pH between about 6.5 and about 9.5 although the pH interval from about 7.5 to about 8.5 is more desirable. The isomerization occurs in the absence of cobalt ion even though the latter may increase enzyme activity. Quite typically the feedstock containing glucose also contains magnesium at a concentration from about 0.1 to about 50 millimoles per liter.

EXAMPLE 4—Glucose Isomerization

The support matrix was a gamma-alumina, 60/80 mesh, impregnated with polyethylenimine and cross-linked with glutaraldehyde so as to furnish pendant aldehyde moieties; see U.S. Pat. No. 4,141,857. Enzyme was immobilized by contacting the support matrix with a solution of glucose isomerase at 4° C. with agitation for about 18 hours. Excess liquid was removed by decantation, and adhering but unbound GI was removed by thorough washing with a saline solution.

To test for the effect of enzyme concentration on immobilization, a total of 1500 units enzyme per gram support matrix was offered at dilutions of 375 and 188 units per ml. There was no significant difference in activity of the resulting immobilized enzyme systems.

A series of immobilized glucose isomerase columns were prepared at different offerings of enzyme, with the results summarized in Table 7.

TABLE 7

| Immobilized Glucose Isomerase | |
|---|---|
| Enzyme Offered units/g | Activity of Immobilized GI, units/g |
| 1500 | 1200 |
| 2000 | 1470 |
| 2500 | 1650 |
| 3000 | 1650 |

The data show that no significant increase occurs in the activity of immobilized GI past an offering of about 2500 units per gram.

The half-life at 60° C. of an immobilized GI was determined from a fixed bed reactor whose feedstock was a solution of 45% by weight purified glucose containing $5 \times 10^{-5}$ molar magnesium ion, 0.1% sodium sulfite, and 0.0007% sodium omadine at a pH of 8.0. The half-life under these conditions was determined to be about 60 days.

What is claimed is:

1. A biologically pure culture of mutant microorganisms of Streptomyces coelicolor having the ability to produce a glucose isomerase in the absence of xylose in an amount at least as great as that produced by the parent microorganism in the presence of xylose, when the microorganisms are grown aerobically in a medium containing an assimilable source of carbon, nitrogen, and mineral nutrients at a temperature from 20° C. to about 45° C.

2. The biologically pure culture of claim 1 where the mutant is Streptomyces coelicolor NRRL 15398.

3. A method of producing a glucose isomerase comprising cultivating Streptomyces coelicolor NRRL 15398 in a nutrient medium for a time sufficient to produce a recoverable quantity of the isomerase.

4. The method of claim 3 where the medium is devoid of xylose.

5. A method of converting glucose to fructose comprising contacting an aqueous solution containing glucose with a glucose isomerase from Streptomyces coelicolor NRRL 15398 at a temperature from about 40° C. to about 80° C. at a pH between about 6.5 and 9.5 for a time sufficient to effect the isomerization of glucose to fructose, and recovering the formed fructose.

6. The method of claim 5 where the temperature is from about 50° C. to about 65° C.

7. The method of claim 5 where the pH is from about 7.5 to about 8.5.

* * * * *